(12) United States Patent
Limaye et al.

(10) Patent No.: US 11,654,239 B2
(45) Date of Patent: May 23, 2023

(54) LOW COST SYRINGE WITH DURABLE AND DISPOSABLE COMPONENTS

(71) Applicant: Becton, Dickinson and Company, Franklin Lakes, NJ (US)

(72) Inventors: Amit Limaye, Wayne, NJ (US); Giridhar Shamsunder, Pittsboro, NC (US); Raghavendranath Ravindranath, Chennai (IN); Amit Kumar, Hyderabad (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 371 days.

(21) Appl. No.: 16/957,639

(22) PCT Filed: Dec. 21, 2018

(86) PCT No.: PCT/US2018/067137
§ 371 (c)(1),
(2) Date: Jun. 24, 2020

(87) PCT Pub. No.: WO2019/133492
PCT Pub. Date: Jul. 4, 2019

(65) Prior Publication Data
US 2020/0324052 A1 Oct. 15, 2020

Related U.S. Application Data

(60) Provisional application No. 62/611,876, filed on Dec. 29, 2017.

(51) Int. Cl.
*A61M 5/31* (2006.01)
*A61M 5/00* (2006.01)
(Continued)

(52) U.S. Cl.
CPC .......... *A61M 5/3129* (2013.01); *A61M 5/002* (2013.01); *A61M 5/31511* (2013.01);
(Continued)

(58) Field of Classification Search
CPC .............. A61M 5/3137; A61M 5/3129; A61M 2005/3142; A61M 2005/3139;
(Continued)

(56) References Cited

U.S. PATENT DOCUMENTS 4,015,709 A 4/1977 Millet
5,211,629 A 5/1993 Pressly et al.
(Continued)

FOREIGN PATENT DOCUMENTS

CN 102316691 A 1/2012
CN 107002730 A 8/2017
WO WO 2016/093661 A1 6/2016

*Primary Examiner* — Theodore J Stigell
*Assistant Examiner* — Rachel T. Smith
(74) *Attorney, Agent, or Firm* — Dickinson Wright PLLC

(57) ABSTRACT

Insulin injection syringes are disclosed that include two types of components, namely, durable components that that do not contact the fluid path and can be reused, and disposable or single-use components that contact the fluid path and are not reused. The durable components do not contact the fluid path so that sterility is not affected. Two different syringe components include a reusable outer sleeve containing scale markings for the syringe and a reusable syringe plunger are provided as durable components in embodiments of the present invention. Syringes manufactured according to the present invention can employ one or both of these durable components. Methods for making, using and packaging such syringes are also disclosed.

14 Claims, 17 Drawing Sheets

(51) Int. Cl.
*A61M 5/315* (2006.01)
*A61M 5/32* (2006.01)
*A61M 5/50* (2006.01)

(52) U.S. Cl.
CPC ............... *A61M 5/32* (2013.01); *A61M 5/50* (2013.01); *A61M 2005/3139* (2013.01); *A61M 2005/3142* (2013.01); *A61M 2205/273* (2013.01); *A61M 2207/10* (2013.01)

(58) Field of Classification Search
CPC .... A61M 5/002; A61M 5/31511; A61M 5/50; A61M 2205/273; A61M 2207/10; A61M 5/3139
See application file for complete search history.

(56) References Cited

U.S. PATENT DOCUMENTS

| | | | |
|---|---|---|---|
| 5,613,952 A | 3/1997 | Pressly, Sr. et al. | |
| 6,402,721 B1* | 6/2002 | Lo | A61M 5/322 604/110 |
| 2002/0088131 A1 | 7/2002 | Baxa et al. | |
| 2008/0086092 A1* | 4/2008 | Loe | A61M 5/1785 250/506.1 |
| 2015/0073354 A1* | 3/2015 | Creaturo | A61M 5/31505 604/189 |

* cited by examiner

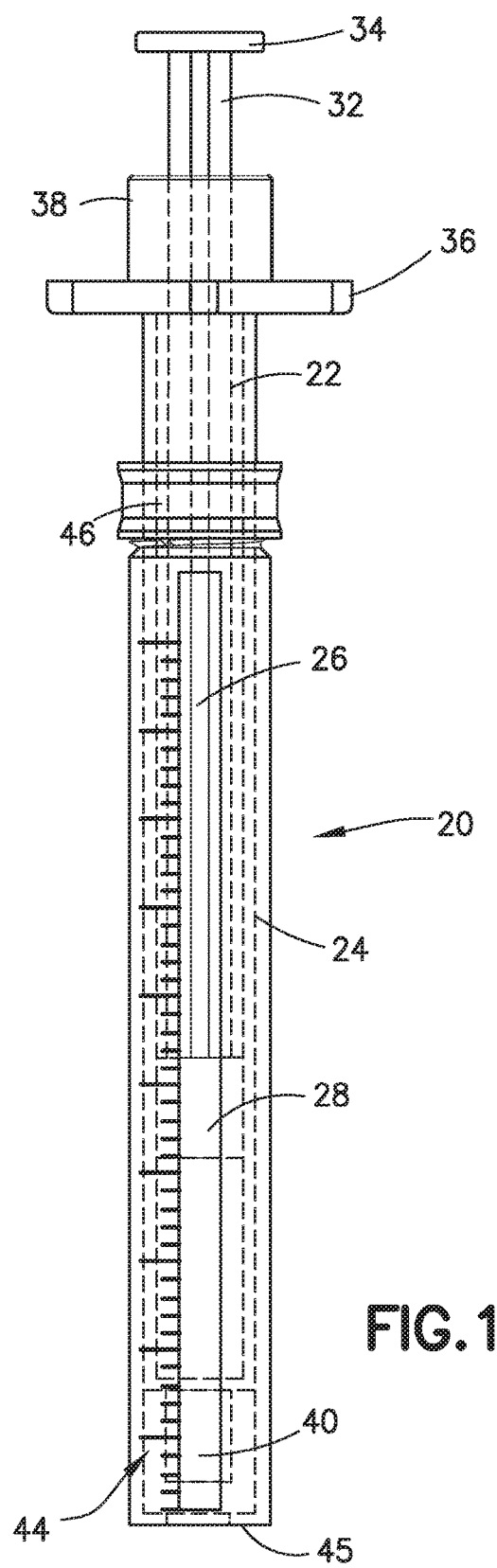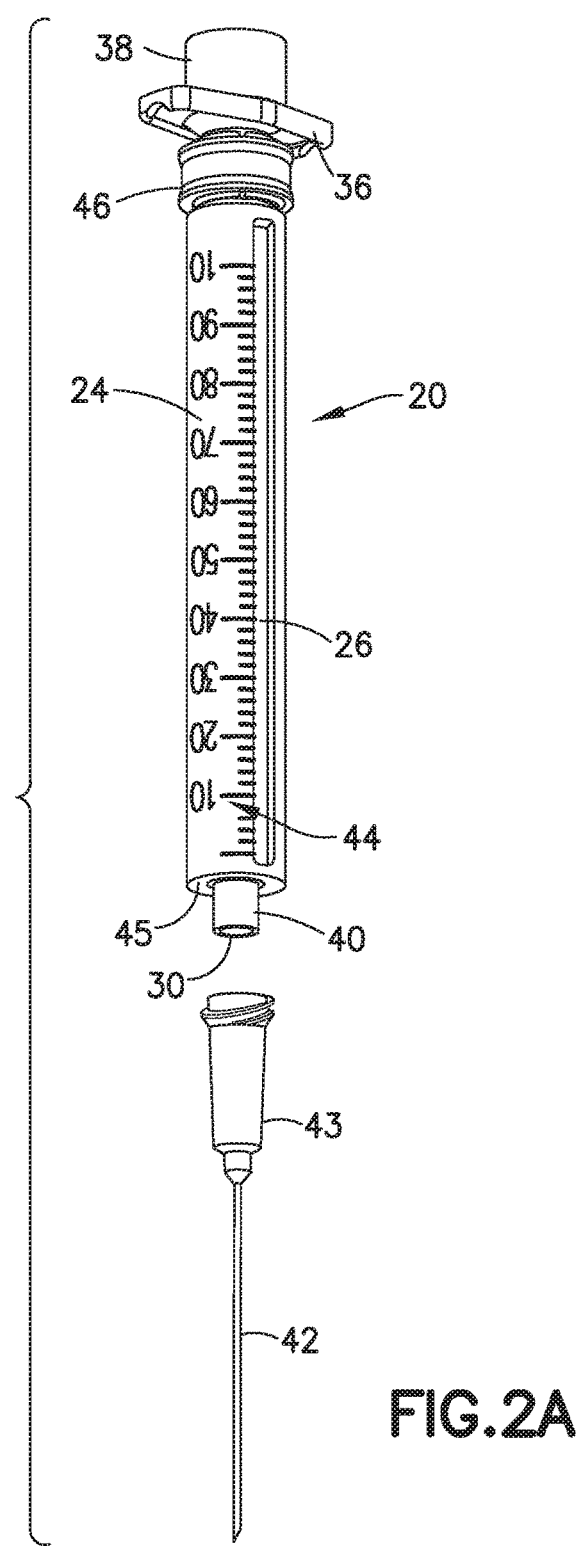

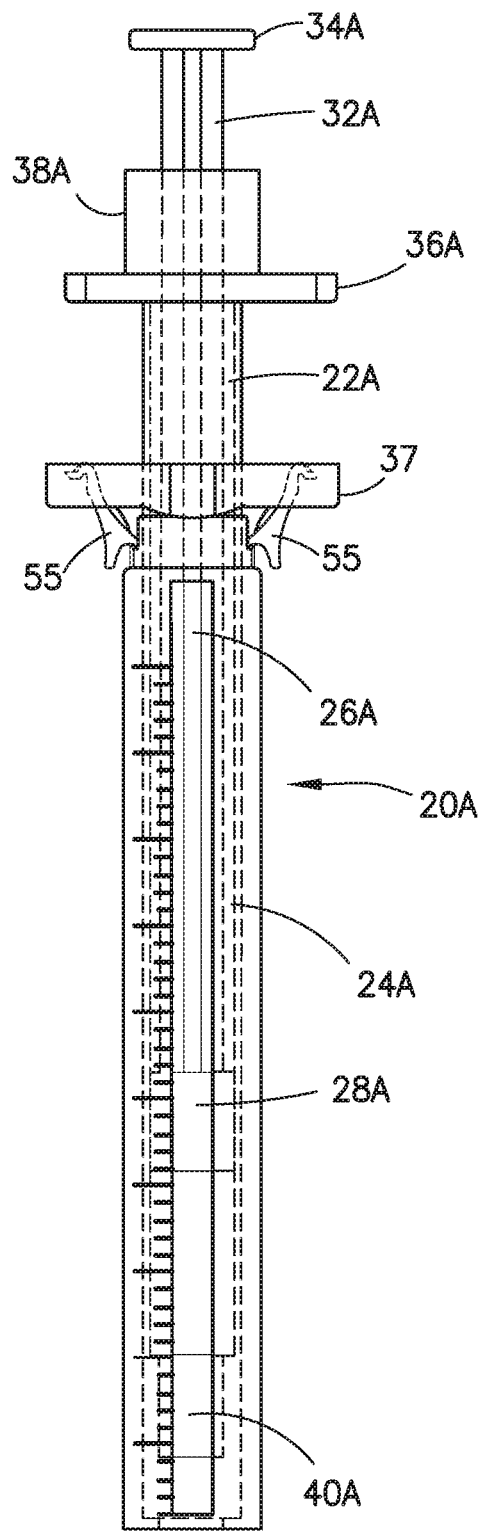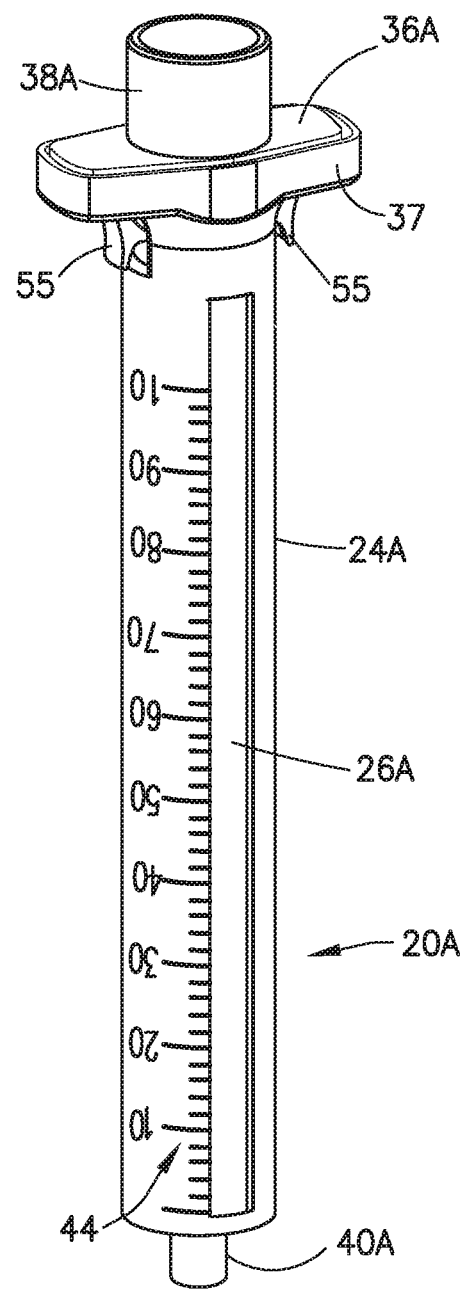
FIG.3
FIG.4A

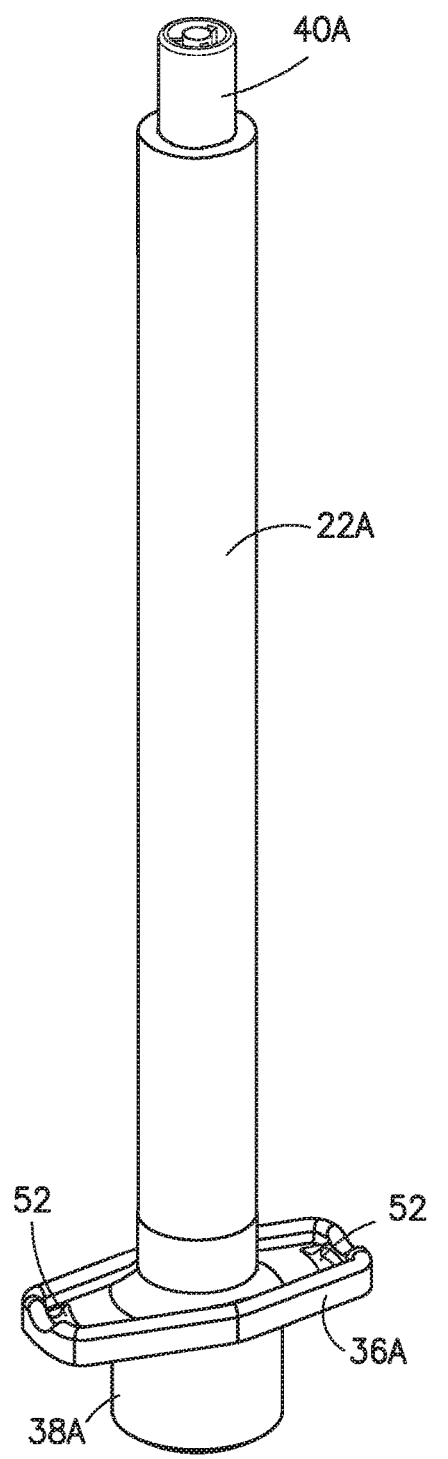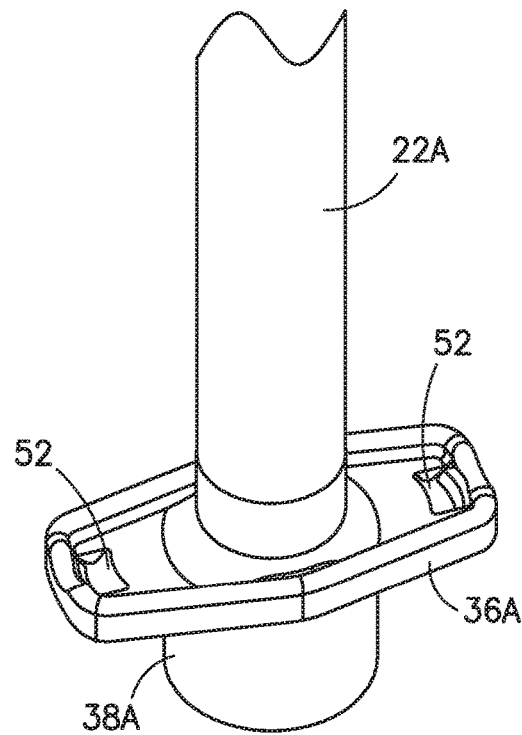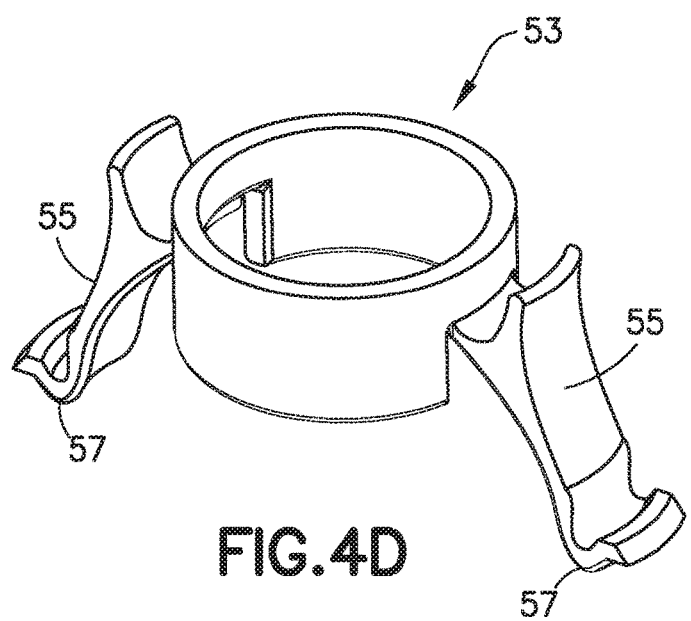
FIG.4B
FIG.4C
FIG.4D

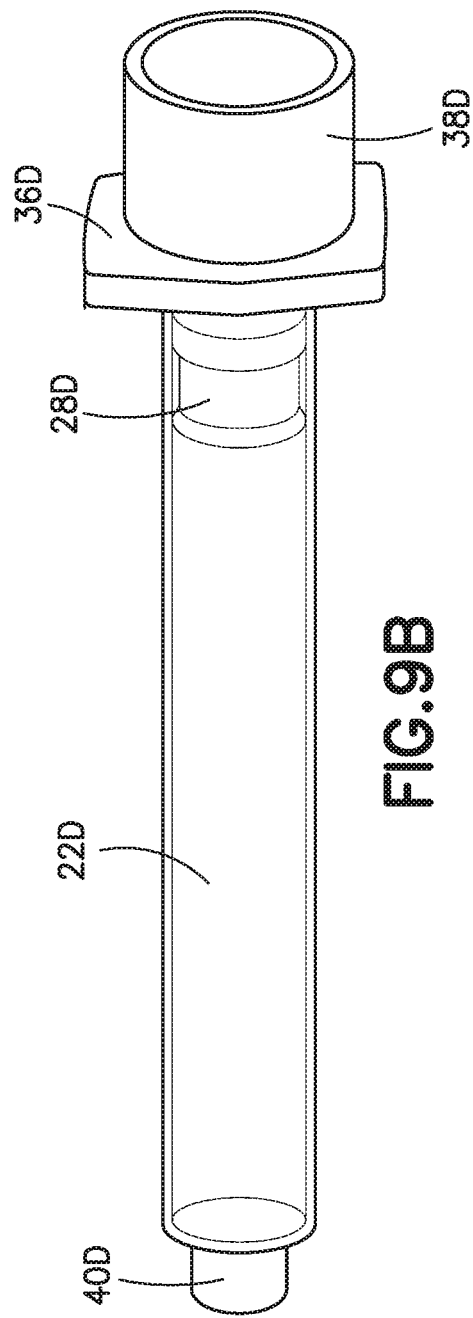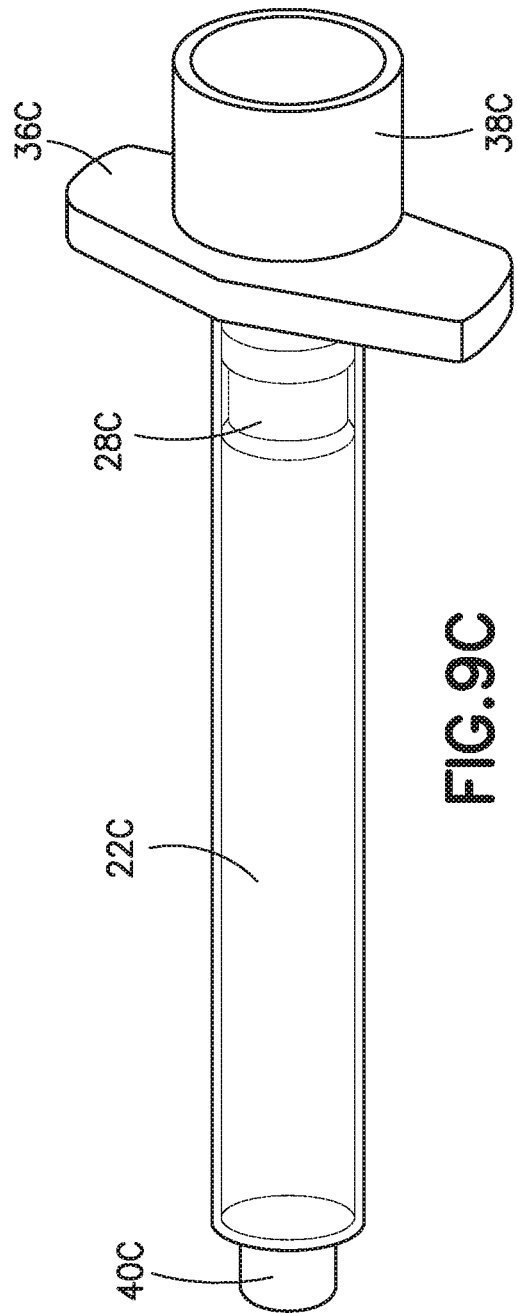

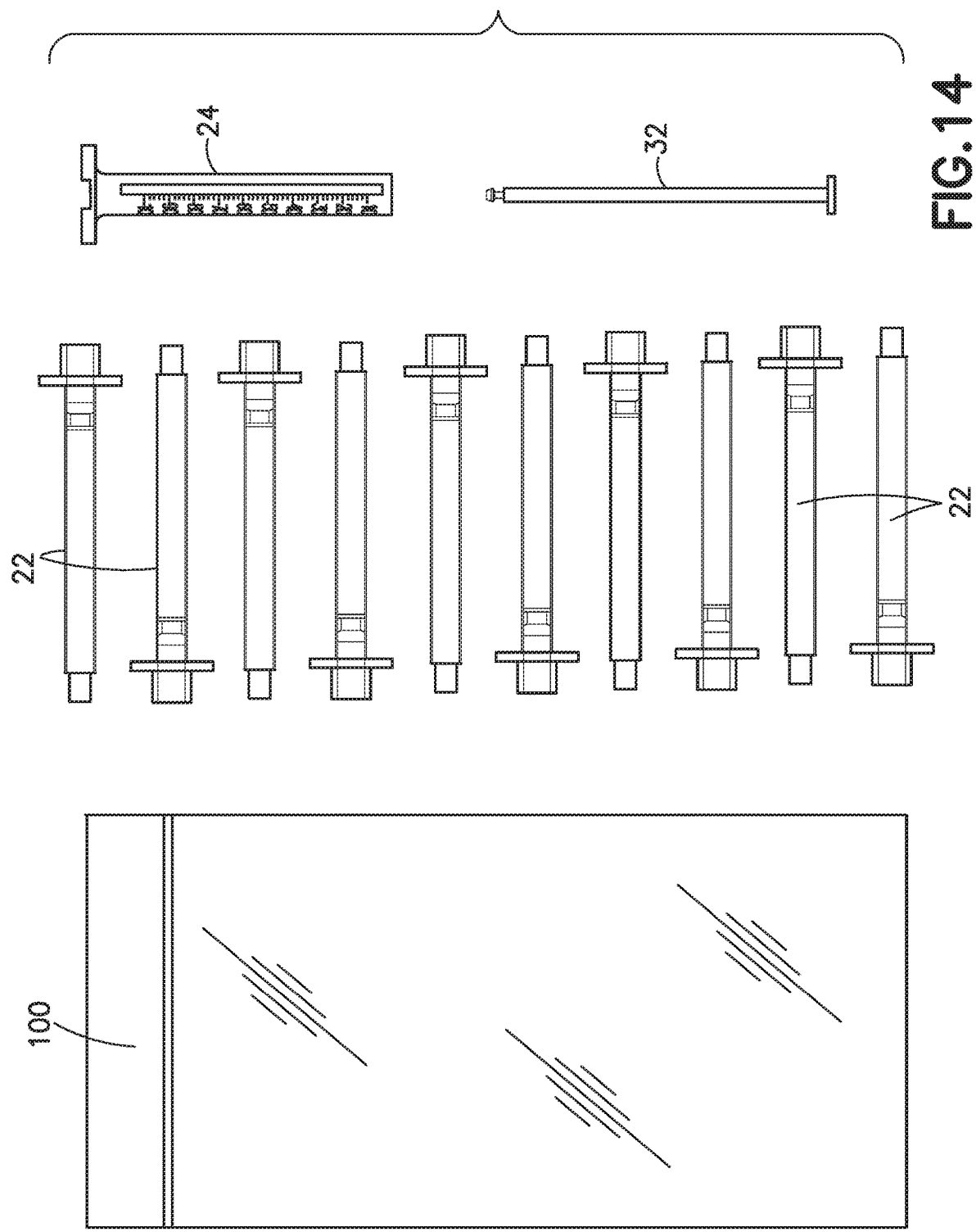

LOW COST SYRINGE WITH DURABLE AND DISPOSABLE COMPONENTS

CROSS-REFERENCE TO RELATED APPLICATION

This application claims priority from U.S. provisional application Ser. No. 62/611,876, filed on Dec. 29, 2017, which is expressly incorporated herein by reference in its entirety.

FIELD OF THE INVENTION

The present invention relates generally to syringes for transferring (i.e., injecting or withdrawing) fluids. In particular, but not by way of limitation, embodiments of the present invention relate to low cost insulin injection syringes in which the low cost is achieved by separating the syringe into two types of components, namely, durable components that that do not contact the fluid path and can be reused, and disposable or single-use components that contact the fluid path and are not reused. Methods for making, using and packaging such syringes are also disclosed and claimed herein.

BACKGROUND OF THE INVENTION

Most syringes in use today are of the disposable or single-use type. A typical disposable syringe is made primarily of plastic and has several key components. The largest, and the one containing the most material, is the plastic barrel. The scale printing on the barrel is a critical and costly assembly step that is needed to assure proper dosing by the user. Inside the barrel is a rubber stopper that is used to create a hermetic seal and displace the liquid medication or other fluid into and out of the barrel. A plastic plunger rod interfaces with the rubber stopper to move it back and forth under the user's control. A metal needle or cannula is usually attached to the distal end of the barrel to allow fluids to be injected into or removed from the body, although this is not always the case. For example, a syringe having a male Luer connector at its distal end can be attached to a female Luer connector on a catheter or IV line to inject or withdraw fluids without the use of a needle or cannula.

In the management of diabetes, disposable plastic syringes are often used to administer liquid insulin to a user several times a day. These single-use syringes typically have clear polymeric barrels with printed scale numbers that allow the user to draw up an accurate dose of insulin from a vial, and fine-gauge metal needles (usually about 6 to 12 mm in length) that inject the dose into the skin with minimal discomfort to the user. The needles may be detachably connected to the barrels using Luer-Lok™ or Luer slip connections, or they may be permanently attached or "staked" to the barrels during manufacture of the syringes. Insulin syringes usually have a capacity of 1 ml or less (with 0.3 ml, 0.5 ml and 1.0 ml barrel sizes being common), with scale markings on the barrel representing units of a specific type of insulin (e.g., U-100 or U-500 insulin). Insulin syringes may also be provided with safety features to prevent reuse of the syringe, to shield the used needle, or both. Because insulin syringes are used only once and a user usually requires several of them each day, they are commonly sold in boxes or bags containing multiple syringes.

In insulin syringes of the type described above, there are no durable (reusable) components. The entire syringe is disposed of after a single use, and none of the components are reused. While disposal of a single-use syringe is advantageous in ensuring sterility and preventing the spread of blood-borne diseases, the expense of providing all of the required syringe components and assembly steps for only a one-time use is higher than might be desired. Discarded syringes also create a disposal burden in hospitals and other medical facilities, since they cannot be mixed with other types of medical waste and must instead be placed in dedicated sharps disposal containers. Therefore, a need exists for a syringe in which the expense and disposal burden associated with one-time use is reduced, while preserving the sanitary advantages of a single-use syringe.

SUMMARY OF THE INVENTION

In accordance with embodiments of the present invention, a low cost syringe is provided by separating the syringe into two types of components, namely, durable components that do not contact the fluid path and can be reused, and disposable or single-use components that contact the fluid path and are not reused. The ability to reuse the durable components reduces the effective per-unit cost of the syringe when multiple syringes are used. Since these components do not contact the fluid path, sterility is not affected. The disposal burden is also reduced because not all of the syringe components need to be disposed of each time a syringe is used.

Two different syringe components—a reusable outer sleeve containing scale markings for the syringe, and a reusable syringe plunger—are provided as durable components in embodiments of the present invention. Syringes manufactured according to the present invention can employ one or both of these durable components.

More specifically, one aspect of the present invention relates to a syringe comprising a barrel assembly having a disposable tubular insert and a reusable outer sleeve, the tubular insert forming a fluid reservoir and having a fluid opening at a distal end thereof, the reusable outer sleeve being detachably received on an outer surface of the tubular insert and having visible scale markings thereon; a stopper movably received in the tubular insert for sealing a proximal end of the tubular insert and for displacing fluid into or out of the tubular insert through the fluid opening upon movement of the stopper within the tubular insert; and a user-operable plunger coupled to the stopper for causing the stopper to move within the tubular insert and thereby displace fluid into or out of the tubular insert through the fluid opening under the control of the user.

In another aspect, the present invention relates to a syringe comprising a disposable portion including a fluid reservoir having a fluid opening at a distal end thereof and a stopper movably received in the fluid reservoir for sealing a proximal end of the fluid reservoir and for displacing fluid into or out of the fluid reservoir through the fluid opening upon movement of the stopper within the fluid reservoir, and a reusable portion comprising a user-operable plunger detachably coupled to the stopper for causing the stopper to move within the fluid reservoir and thereby displace fluid into or out of the fluid reservoir through the fluid passage under the control of the user.

Additional aspects of the invention relate to methods for using syringes of the type described for transferring fluids, and syringe multipacks in which the durable and disposable components of the syringe are packaged for sale or use.

BRIEF DESCRIPTION OF THE DRAWINGS

Aspects and advantages of embodiments of the invention will be more readily appreciated from the following detailed description, taken in conjunction with the accompanying drawings, in which:

FIGS. 1 and 2A-2D illustrate a syringe according a first embodiment of the invention, which employs a collar lock between a disposable tubular insert and a reusable outer sleeve;

FIGS. 3 and 4A-4F illustrate a syringe according a second embodiment of the invention, which employs a side lock between the disposable tubular insert and the reusable outer sleeve;

FIGS. 9B and 9C illustrate the disposable tubular inserts used in the syringe embodiments of FIG. 9A and FIGS. 7-8, respectively;

FIG. 14 illustrates the manner in which multiple syringe assemblies according to any of the previous embodiments can be packaged for sale or use.

DETAILED DESCRIPTION OF EMBODIMENTS OF THE PRESENT INVENTION

Figures 2B, 2C:
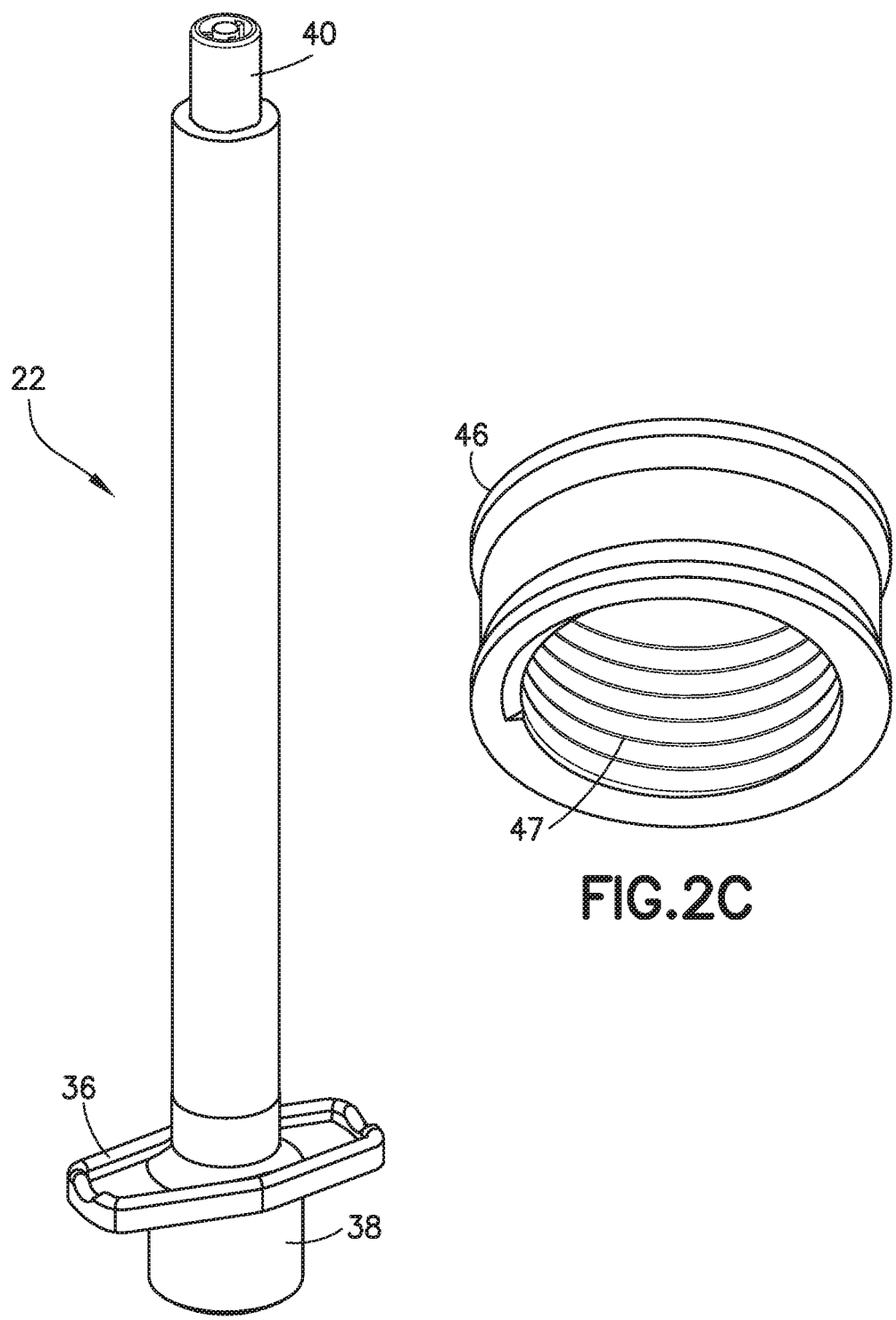
Figure 2D:
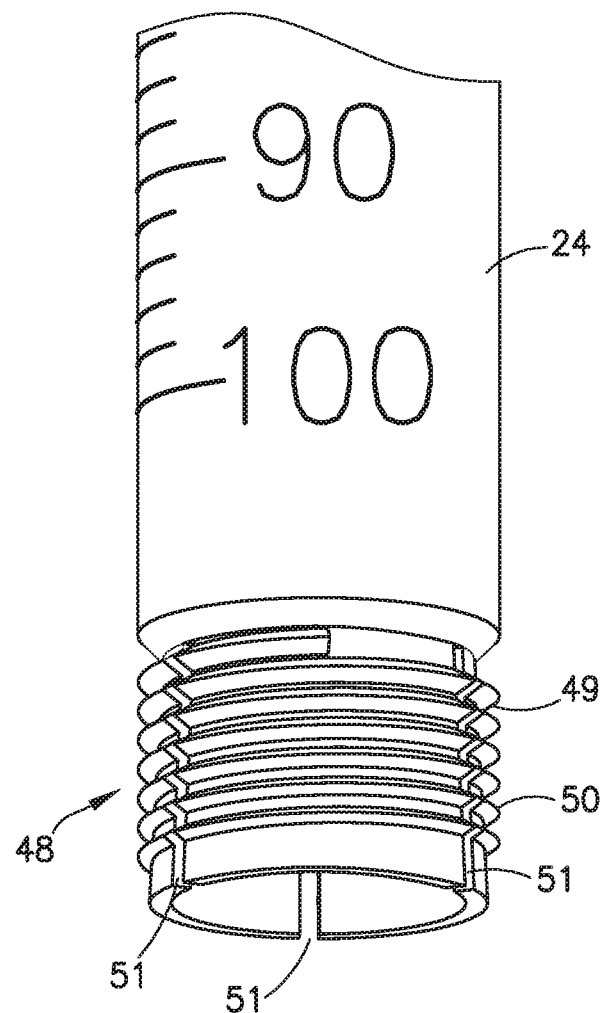
Figure 4F:
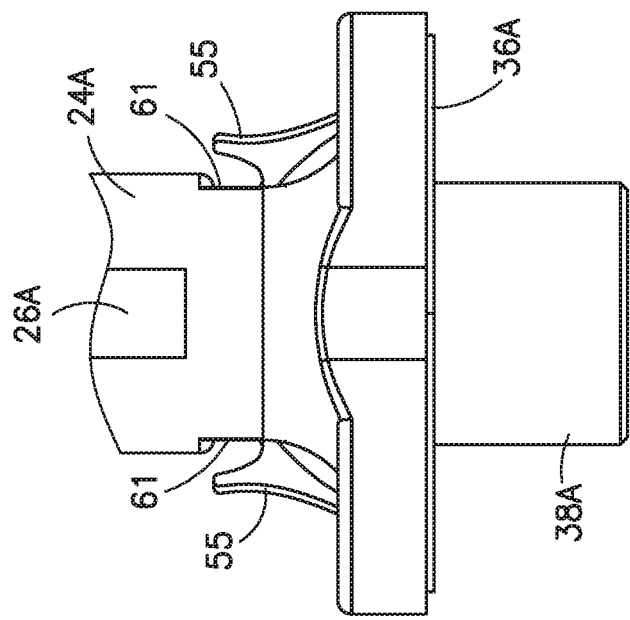
Figure 4E:
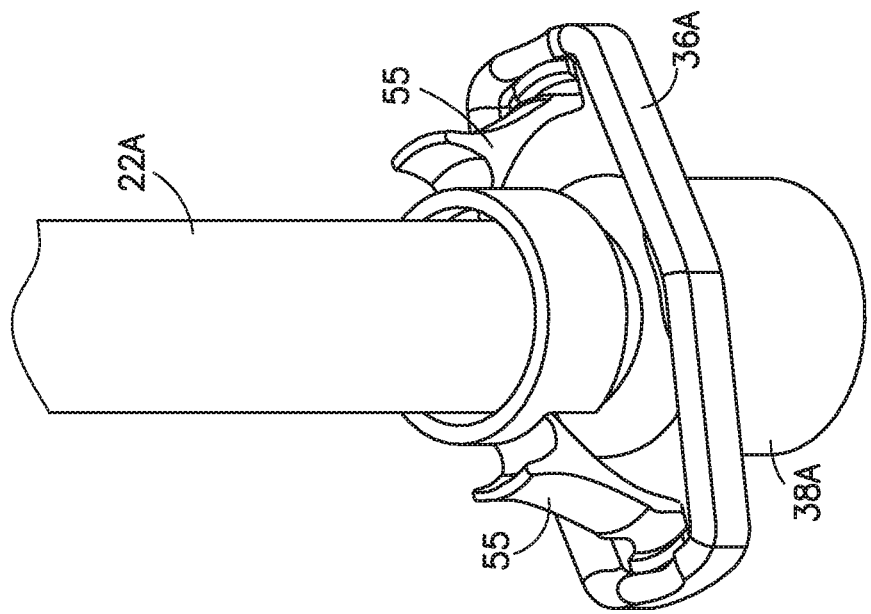

Reference will now be made in detail to embodiments of the present invention, which are illustrated in the accompanying drawings, wherein like reference numerals refer to like elements throughout. The embodiments described and illustrated herein exemplify, but do not limit, the present invention, and the drawings are not necessarily to scale with respect to each other or with respect to actual physical embodiments. Further, it will be understood by one skilled in the art that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as "up", "down", "bottom", "top", "distal" and "proximal" are relative, and are employed to aid illustration, but are not limiting.

FIGS. 1 and 2A-2D illustrate a syringe 20 according a first embodiment of the invention. The syringe 20 comprises a tubular barrel assembly that includes a disposable tubular insert 22 and a reusable outer sleeve 24 that is open at both ends and coaxially receives the insert 22. The disposable tubular insert is preferably made of a plastic (polymeric) material, such as polypropylene, that can be inexpensively injection molded. The reusable outer sleeve 24 is preferably also made of a plastic material, such as polypropylene, polystyrene, polycarbonate or ABS, but can also be made of a metal such as stainless steel. In general, it is preferred that the reusable outer sleeve 24 be made from a relatively stiff and durable material, whereas the disposable insert 22 can be made from a thinner, less rigid material. The upper portion of the tubular insert 22 can be seen in the partially disassembled view of FIG. 1. The lower portion of the tubular insert 22 is partially obscured by the outer sleeve 24 in FIG. 1, but is visible through an elongated rectangular slot 26 formed lengthwise in the outer sleeve 24. FIG. 2A shows the tubular insert 22 fully received in the outer sleeve 24 as would be the case during use of the syringe 20.

The tubular insert 22, which is shown alone in FIG. 2B, is designed to be disposable and forms a fluid reservoir for the fluid (not shown) that is to be injected or withdrawn by the syringe 20. The volume of the fluid reservoir varies according to the position of a separate rubber stopper 28 which seals the proximal end of the insert 22. The stopper 28 is movably received in the tubular insert 22 for displacing fluid into or out of the tubular insert 22 through a fluid opening 30 at the distal end of the tubular insert 22.

A plastic plunger 32 (shown in FIG. 1 but omitted from FIGS. 2A and 2B) having its distal end connected to the stopper 28 causes the stopper 28 to move up or down within the tubular insert 22 and thereby displace fluid into or out of the tubular insert 22 through the fluid opening 30 under the control of the user. A thumb press 34 integrally formed at the proximal end of the plunger 32 allows the user to pull or push on the plunger 32 as required. A flange 36 with opposed arms is integrally formed near the proximal end of the tubular insert 22 and can be held by a user's fingers when operating the plunger 32. An annular collar 38 is integrally formed at the proximal end of the tubular insert 22, above the flange 36, to receive a removable sterile cap (not shown) that covers the proximal end of the syringe 20 before use. With the plunger 32 fully depressed, the thumb press 34 is slightly elevated above the collar 38 so that the thumb press 34 can be grasped to operate the plunger 32.

In the embodiment shown, the fluid opening 30 is formed in a reduced diameter distal end portion 40 of the tubular insert 22 which is intended to receive a permanently attached or "staked" needle or cannula (not shown). The use of a staked needle can be advantageous in reducing fluid dead space within the insert 22. Alternatively, the distal end portion 40 can be formed as a male Luer slip or Luer Lok™ connector which allows the tubular insert 22 to be affixed to a separately provided needle or cannula 42 via a hub 43. The Luer connector can also be used to couple the syringe 20 directly to a female Luer connector on a catheter or IV line without the use of a needle or cannula. In the case of a Luer Lok™ connector, the tapered Luer tip can be formed integrally with the insert 22, and the internally threaded locking collar can be formed integrally with the sleeve 24. Alternatively, both portions can be formed integrally with the insert 22. Another possibility is to provide a snap fit between the hub 43 and the reduced diameter distal end portion 40 of the tubular insert, in lieu of a Luer connection. Whether separate or permanently affixed, the needle or cannula may have a sharp tip for penetrating the skin or a pro re nata (PRN), or it may consist of a blunt cannula of the type used to access a needleless connector.

For cost reasons, the disposable tubular insert 22 is preferably devoid of any printed indicia that require separate manufacturing steps, including the printed scale markings that are typically needed for proper operation of the syringe 20. Instead, the required scale markings 44 are provided on the outer sleeve 24, which can be detached from the used syringe 20 and reused. The scale markings 44 on the outer sleeve 24 may take the form of a combination of lines and numerals representing milliliters or units of insulin, as shown in FIGS. 1 and 2, or any other suitable form as may be required for the specific application. The scale markings 44 may be ink-printed or laser-printed, embossed, engraved, laser-etched, or a combination of these (e.g., embossed with an ink-printed overlay for increased legibility). The embossing or engraving may be accomplished as part of the injection molding process that is used to manufacture the outer sleeve 24 (if it is made of plastic), with any desired ink-printing carried out during a separate manufacturing step.

The lengthwise slot 26 in the outer sleeve 24 allows the user to directly view the tubular insert 22, which is transparent or translucent, so that the fluid level in the tubular insert 22 can be viewed and compared with the scale markings 44 on the outer sleeve 24. Due to the presence of the slot 26, the outer sleeve 24 can be made partially or completely opaque if desired, although it will normally be preferable to make the outer sleeve 24 transparent or translucent so that the fluid level can be seen to some extent through its walls (although perhaps less clearly than through the slot 26). The slot 26 can be omitted if the outer sleeve 24 is made sufficiently transparent or translucent so that the fluid level in the tubular insert 22 can be seen through the walls of the outer sleeve 24 with enough precision for proper dosing. Alternatively, the slot 26 can be replaced by a transparent or translucent window in embodiments where the outer sleeve 24 is partially or completely opaque.

A detachable connection is provided between the disposable tubular insert 22 and the reusable outer sleeve 24 so that the two components can be coupled together and used in the same manner as a conventional syringe, and then separated to allow for reuse of the outer sleeve 24. This connection can be a simple friction or press fit between all or portions of the cylindrical outer surface of the tubular insert 22 and the cylindrical inner surface of the outer sleeve 24, or a clamshell connection if the sleeve 24 is split or hinged. However, given the importance of axially positioning the scale markings 44 in such a way that they accurately and consistently represent the correct fluid volume within the tubular insert 22, a more precise and positive releasable locking arrangement will usually be desired. The locking function is primarily needed in the axial direction because that is the direction in which the fluid level is compared with the scale markings 44, but in some applications rotational locking (i.e., prevention of relative rotation between the tubular insert 22 and the outer sleeve 24) may also be needed or desired.

One axial locking arrangement, referred to as a collar lock, is shown in FIGS. 1 and 2A-2D. In this arrangement, the tubular insert 22 bottoms out on an annular lip 45 formed at the bottom of the sleeve 24 when it reaches its full insertion point within the sleeve. At this point a separate collar 46 with internal threads 47, which is received on an externally threaded proximal end portion 48 of the sleeve 24, is rotated so that it advances from a location 49 on the sleeve 24 to a slightly more proximal location 50. The threaded end portion 47 has a slightly greater outside diameter at the location 50 than it does at the location 49. Cuts or gaps 51 divide the proximal end portion 48 into three or more portions which are relatively flexible. When the collar 46 is rotated to the location 50, the increasing diameter of the threaded end portion 47 causes these flexible portions to be squeezed inwardly to grip the insert 22 and thereby lock the sleeve 24 and the insert 22 to each other both axially and rotationally. In an alternative embodiment, the threaded end portion 47 has a slightly greater outside diameter at the location 49 than it does at the location 50, and the collar 46 is rotated so that it advances from the location 50 to the location 49 to secure the sleeve 24 to the insert 22.

The user initially receives the syringe 20 with the outer sleeve 24 either already attached or provided as a separate component which the user attaches to the insert 22 before use. If a needle or cannula 42 is required for the intended fluid transfer but is not pre-affixed or pre-attached to the insert 22, the user also attaches the required needle or cannula. The user then performs the fluid transfer, which may consist of a fluid aspiration (e.g., of insulin from a vial), an injection of fluid into the body, a delivery of fluid into a catheter or IV line, or a withdrawal of fluid from the body (e.g., a blood sample), or some combination of these steps. In doing so, the user can observe the amount of fluid in the syringe 20 by comparing the fluid level that is visible through the slot 26 with the scale markings 44 on the outer sleeve 24. When the fluid transfer is complete, the user removes the outer sleeve 24 by unscrewing the collar 46 and discards the remaining portion of the syringe 20. The outer sleeve 24 and collar 46 can then be reused as part of another syringe 20 by attaching it to another insert 22 and repeating the steps above.

Several advantages of the disclosed syringe 20 will be apparent. For example, there is a reduction in the effective per-unit cost of the syringe (perhaps up to 25%) because a labor intensive manufacturing step (printing of the scale markings) is performed on a component of the syringe 20 (the outer sleeve 24) that can be used multiple times before being discarded. Such reuse does not compromise the sterility of the syringe because the outer sleeve 24 and collar 46 do not come into contact with body fluids or with the fluid being transferred by the syringe 20. Another advantage is that the reusable outer sleeve 24 can be made of a sufficiently rigid material, such as polycarbonate or even metal, to reduce the rigidity required of the insert 22. In other words, the walls of the insert 22 can be made thinner than would otherwise be required to withstand handling by the user and the internal fluid pressures generated by an injection, because the insert 22 is snugly received in a closely conforming sleeve 24 that can provide some of the required strength. This results in less waste of material when the insert 22 is discarded than would be the case for the barrel of a conventional single-use syringe.

FIGS. 3 and 4A-4F illustrate a syringe 20A according a second embodiment of the invention (the needle or cannula 42 is not shown in this or subsequent embodiments, but will typically be present). The syringe 20A is constructed in much the same manner as the syringe 20 of FIGS. 1 and 2, except that a different locking arrangement is provided between the disposable tubular insert 22A and the reusable outer sleeve 24A. In particular, the flange 36A of the insert 22A is received in the cavity of a correspondingly shaped receptacle 37 formed at the proximal end of the sleeve 24A. In use, the flange 36A and the adjoining receptacle 37 together form a combined flange that can be held by the user's fingers. The underside of the flange 36A has a distally facing cavity with a pair of shallow indents 52 (visible in FIGS. 4B and 4C) that interface with a sleeve collar 53 (shown alone in FIG. 4D). The sleeve collar 53 is captured and affixed within the sleeve 24A and the receptacle 37, and has two protruding, cantilevered, proximally extending arms 55 that are flexible and normally biased outwardly. One end 57 of each arm 55 engages a corresponding indent 52 of the flange 36A, while the other end protrudes through an aperture 61 (visible in FIG. 4F) in the sleeve 24A. The engagement of the ends 57 of the arms 55 with the indents 52 in the flange 36A locks the sleeve 24A and the insert 22A to each other both axially and rotationally. The sleeve 24A and the insert 22A can be separated from each other after the syringe 20A is used by squeezing the arms 55 inwardly to disengage the ends 57 of the arms from the indents 52, and then pulling the sleeve 24A and insert 22A apart.

Figure 5:
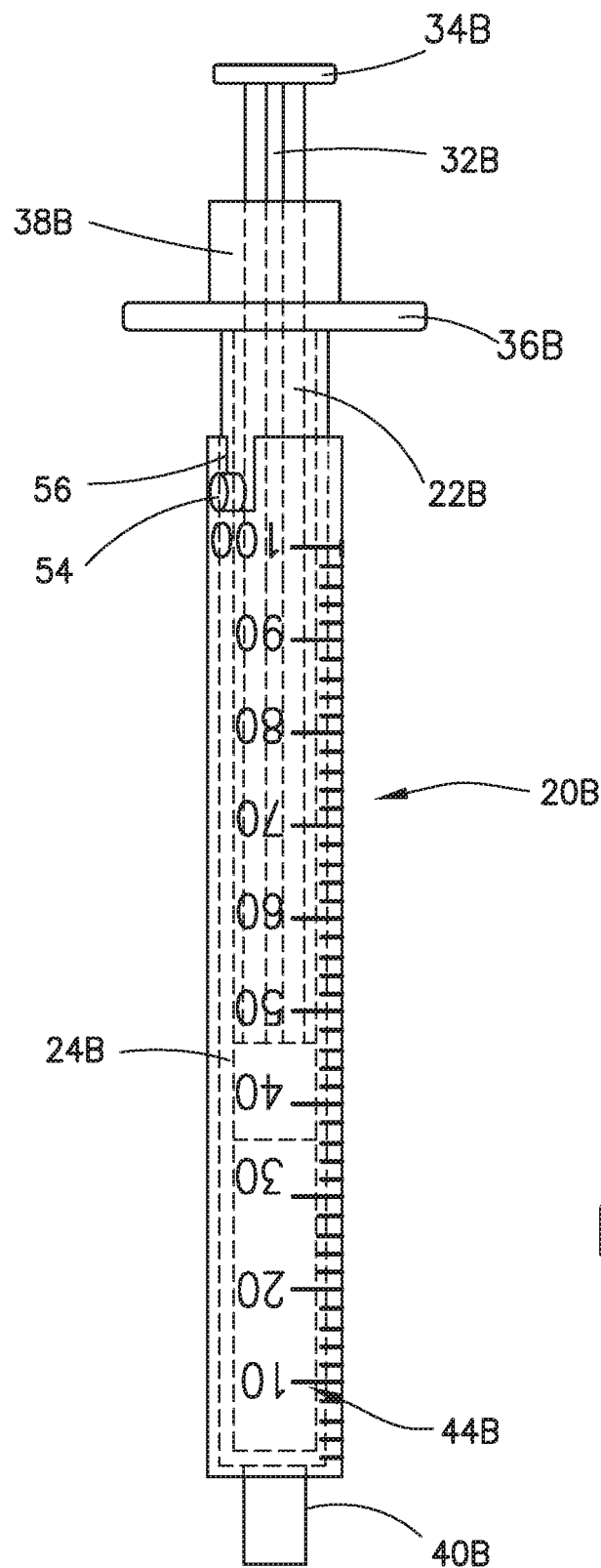
FIGS. 5 and 6 illustrate a syringe according a third embodiment of the invention, which employs a bayonet lock between the disposable tubular insert and the reusable outer sleeve.
Figure 6:
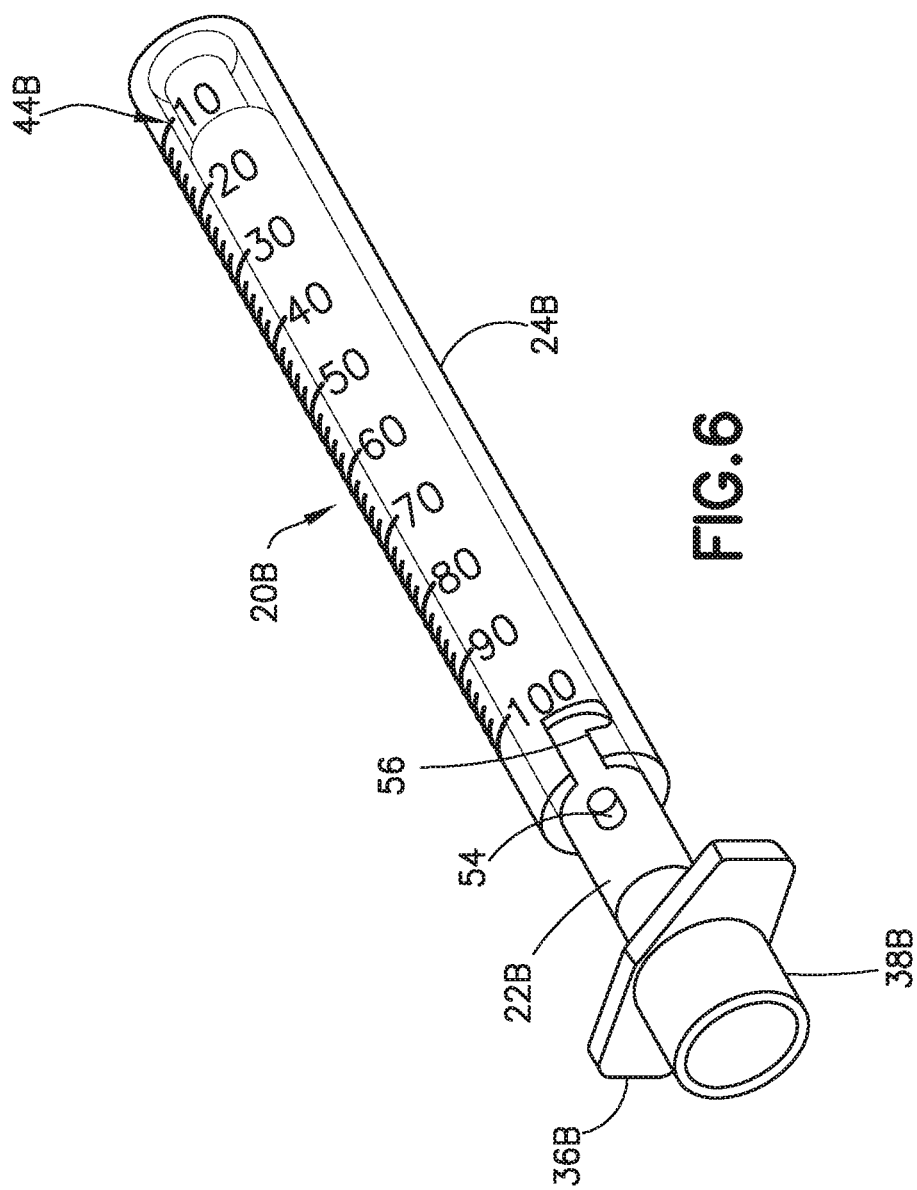

FIGS. 5 and 6 illustrate a syringe 20B according a third embodiment of the invention. The syringe 20B is constructed in much the same manner as the syringes 20 and 20A of FIGS. 1-4F, except that a different locking arrangement is provided between the disposable tubular insert 22B and the reusable outer sleeve 24B. In particular, the insert 22B is molded with a laterally extending lug or projection 54, and a proximal portion of the reusable outer sleeve 24B has an open-ended, L-shaped bayonet slot 56 for slidably receiving the projection 54 to detachably secure the sleeve 24B to the insert 22B by a combination of axial and rotational movement. The bayonet connection provides both axial and partial rotational locking between the sleeve 24B and the insert 22B, and can be released by rotating and axially displacing these two components in the reverse direction with respect to each other. This allows the sleeve 24B and the insert 22B to be separated from each other after the syringe 20B is used so that the sleeve 24B can be reused.

Figure 7:
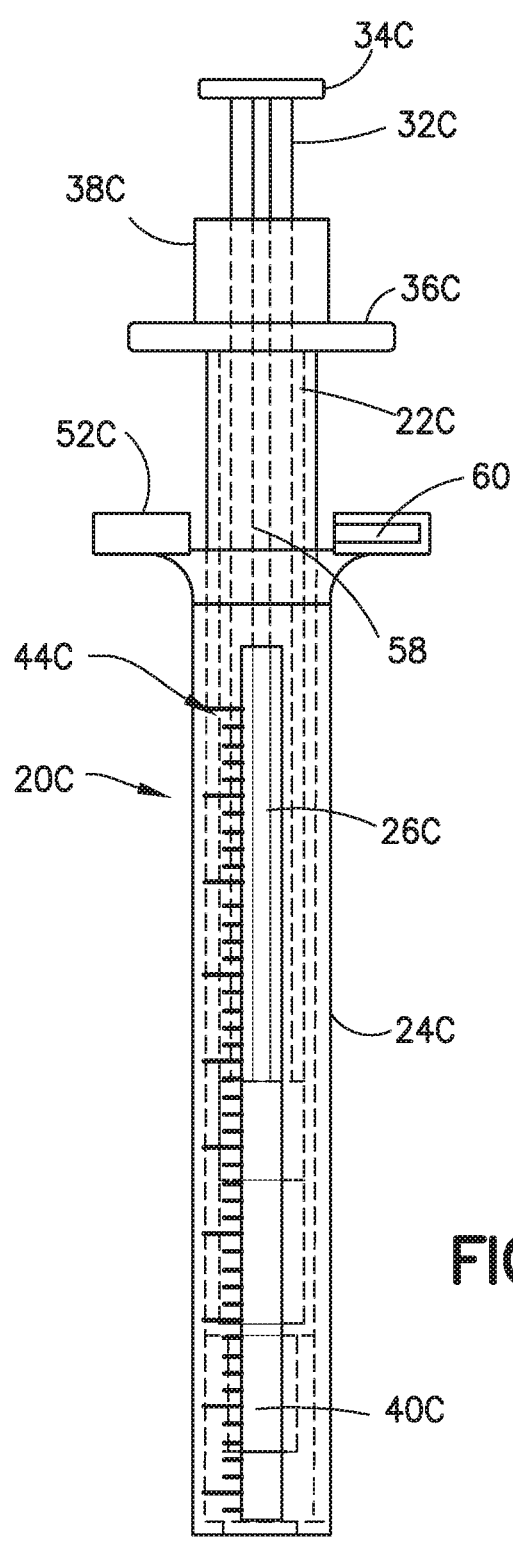
FIGS. 7 and 8 illustrate a syringe according a fourth embodiment of the invention, which employs a twist lock between the disposable tubular insert and the reusable outer sleeve.
Figure 8:
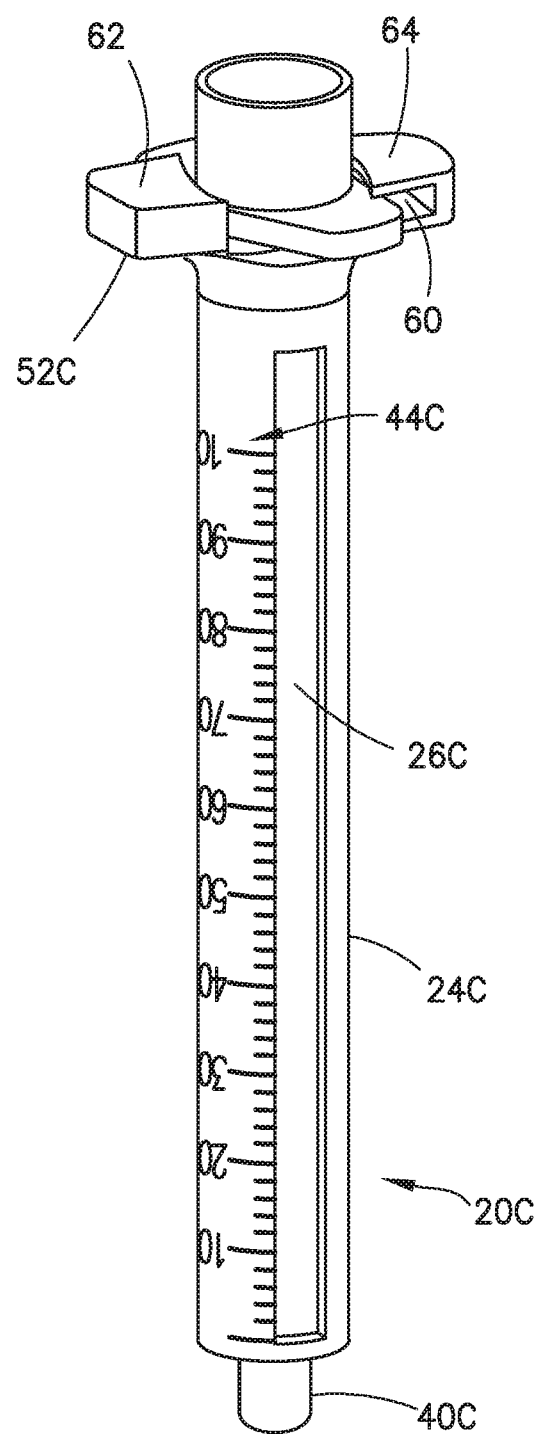

FIGS. 7 and 8 illustrate a syringe 20C according a fourth embodiment of the invention. In this embodiment, the flange 36C of the insert 22C is received in the cavity of a correspondingly-shaped receptacle 52C formed at the proximal end of the sleeve 24C. The receptacle 52C has slots 58 in its front and rear sidewalls to receive the arms of the flange 36C when the insert 22C is rotated 90 degrees and depressed relative to the sleeve 24 from the position shown in FIG. 7 to the position shown in FIG. 8. The receptacle 52C also has diagonally opposed side openings 60 in its front and rear walls to frictionally receive and retain the arms of the flange 36C when the insert 22C is rotated an additional 90 degrees relative to the sleeve 24 from the position shown in FIG. 8. Top closures 62, 64 are located over the side openings 60 to prevent the insert 22C from being axially withdrawn from the sleeve 24C following this second 90 degree rotation, and the closed sidewalls of the receptacle 22C prevent any further-rotation of the insert 22C in the same direction. In this way, the insert 22C is locked both axially and rotationally within the sleeve 24C. The frictional engagement between the arms of the flange 36C and side openings and walls of the receptacle 52C can be augmented, if desired, by providing mating or interlocking structures (not shown) on these structures. The flange 36C and the adjoining receptacle 52C together form a combined flange that can be held by the user's fingers during use of the syringe 20C. The insert 22C and the sleeve 24C can be separated from each other after use of the syringe 20C by first rotating and then axially displacing them with respect to each other in the reverse directions. This allows the sleeve 24C to be reused and the remainder of the syringe 20C to be disposed of.

Figure 9A:
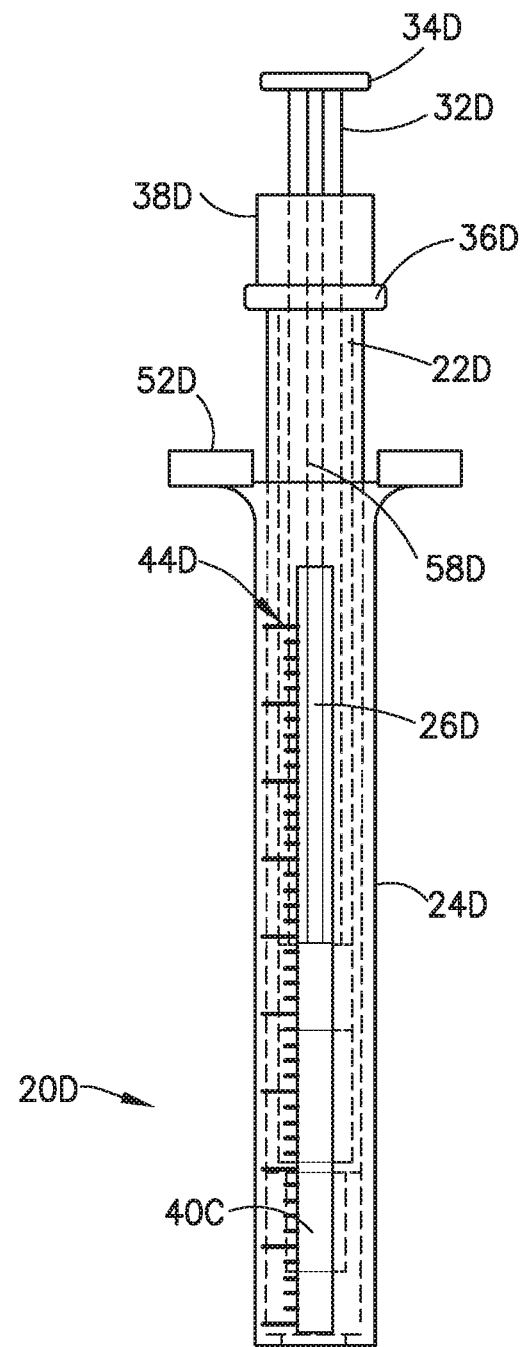
FIG. 9A illustrates a modified version of the syringe shown in FIGS. 7 and 8.
Figure 9D:
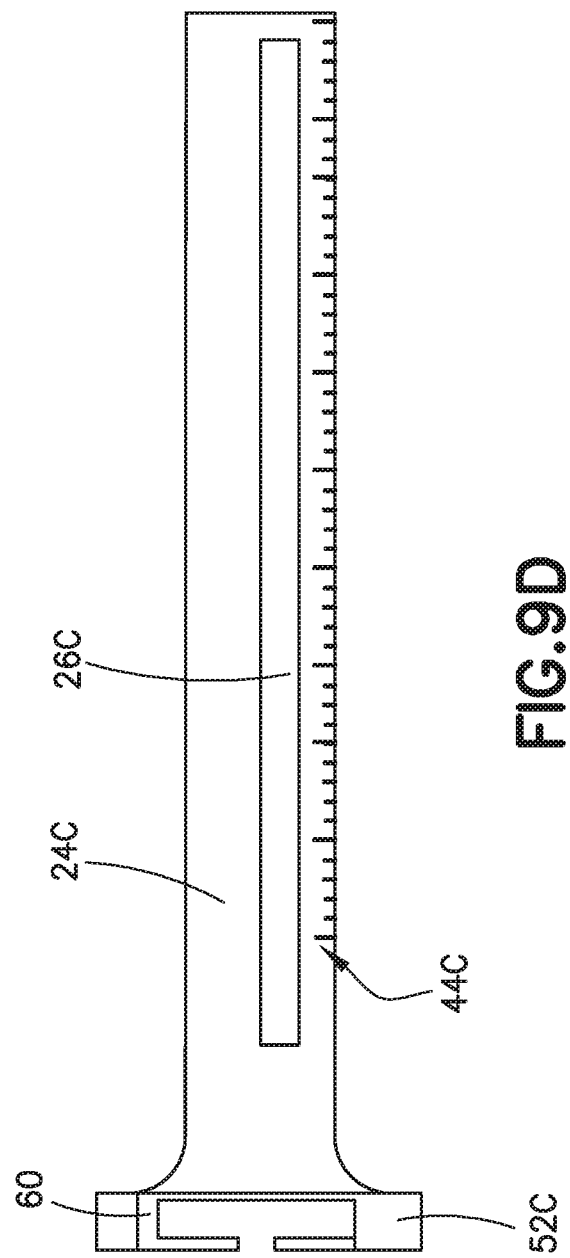
FIGS. 9D and 9E are front and back views of the reusable outer sleeve used in the syringe embodiment of FIGS. 7-8.
Figure 9E:
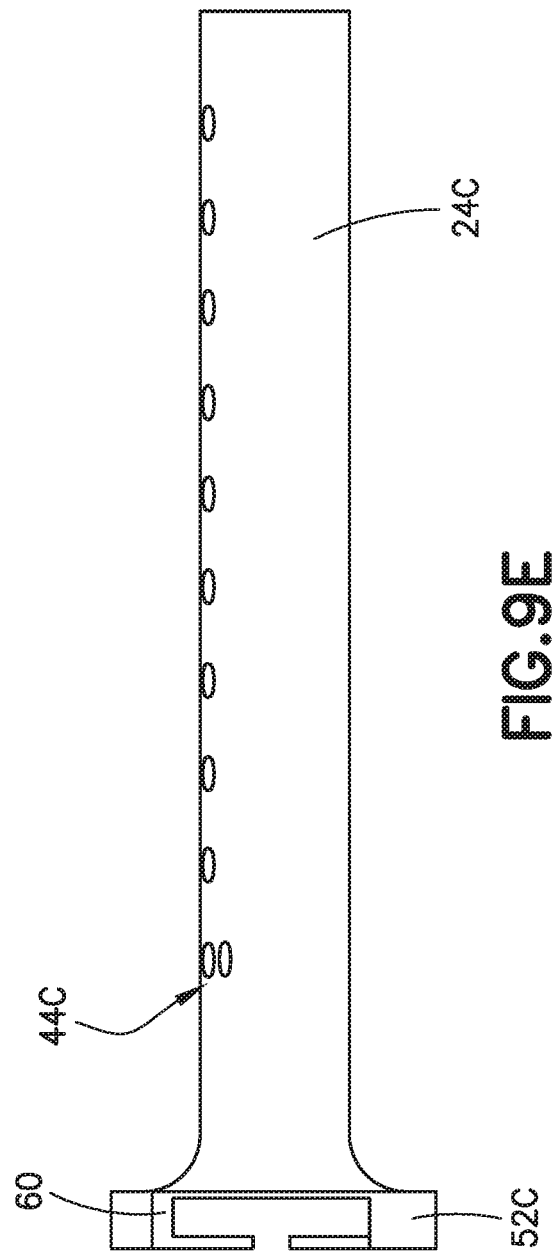
Figure 10:
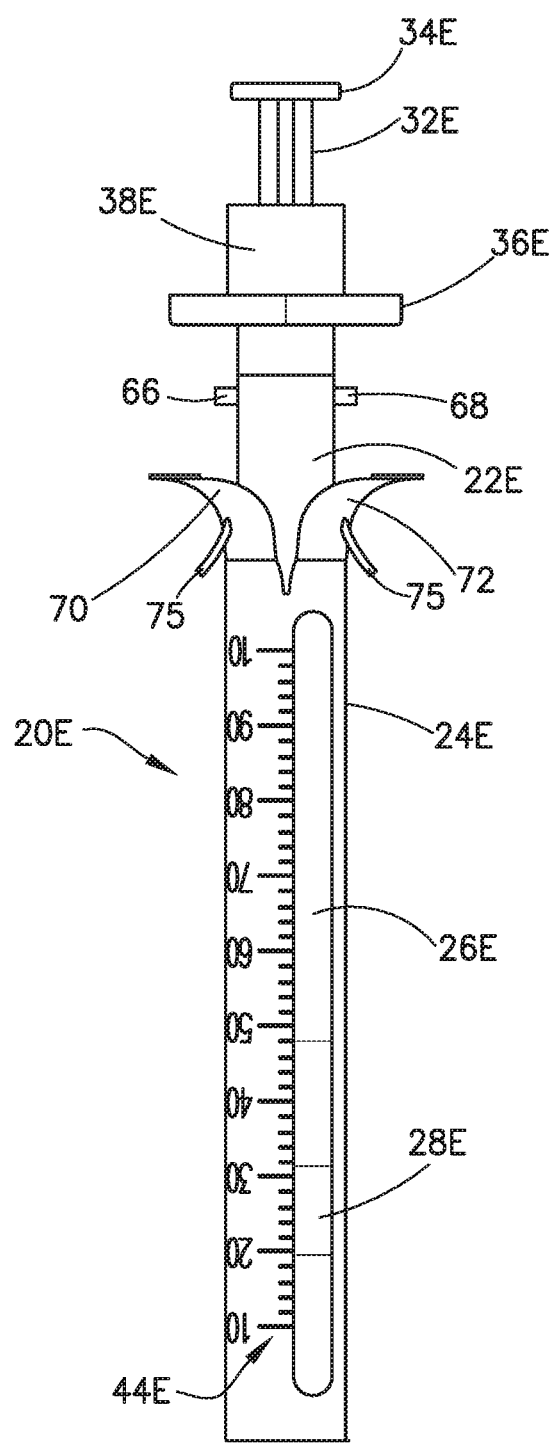
FIGS. 10 and 11A-11D illustrate a syringe according a fifth embodiment of the invention, which employs a press lock between the disposable tubular insert and the reusable outer sleeve.
Figure 11A:
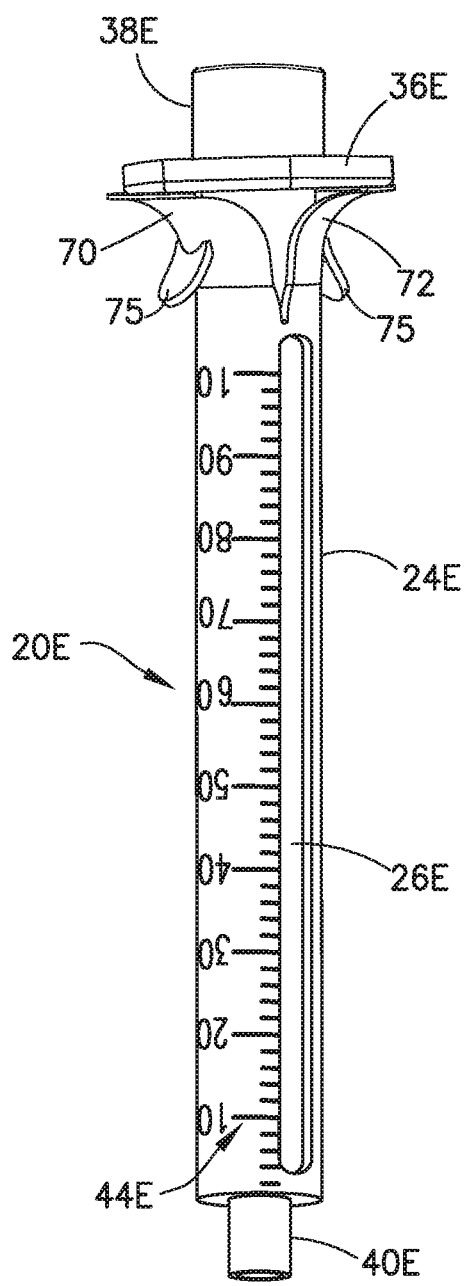
Figure 11D:
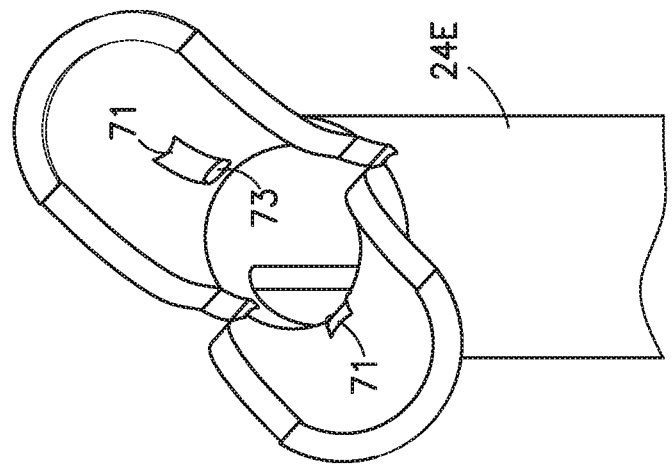
Figure 11C:
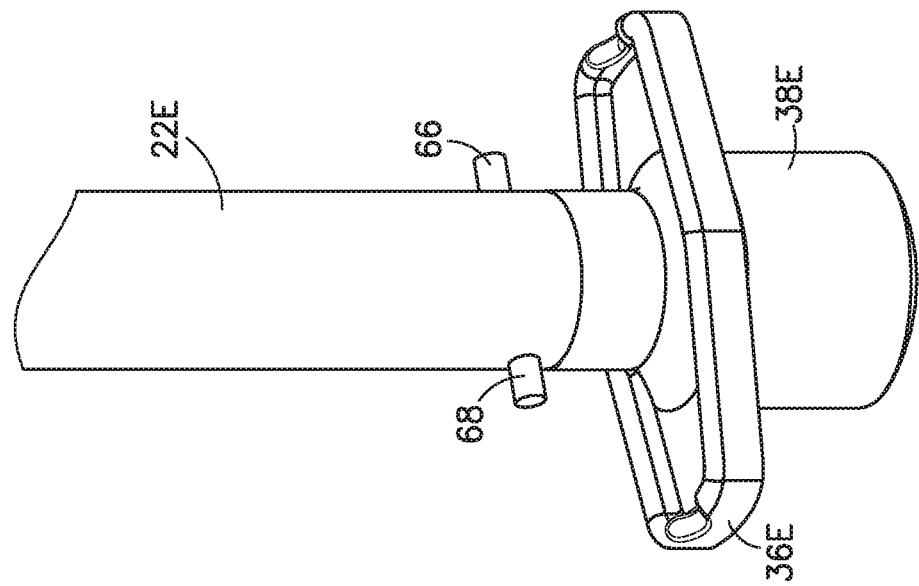
Figure 11B:
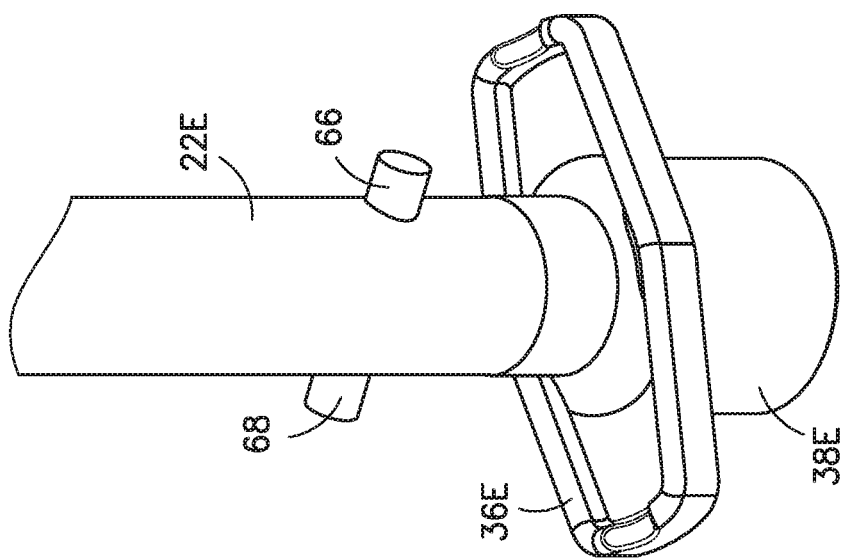

The embodiment of FIG. 9A is similar to that of FIGS. 7 and 8, except that the length of the flange 36D is reduced (truncated) to save additional material in the manufacture of the insert 22D. FIG. 9B shows the insert 22D of FIG. 9A removed from the outer sleeve 24D and more clearly illustrates the reduced length of the flange 36D. For comparison, FIG. 9C shows the insert 22C of FIGS. 7 and 8 with the full length flange 36C. FIGS. 9D and 9E are front and back views of the reusable outer sleeve 24C of FIGS. 7 and 8 as it would appear when removed from the disposable insert 22C. The reusable outer sleeve 24D of FIG. 9A would have essentially the same appearance.

FIGS. 10 and 11A-11D illustrate a syringe 20E according a fifth embodiment of the invention. The syringe 20E is constructed in much the same manner as the syringes 20-20D of FIGS. 1-9E, except that a different locking arrangement is provided between the disposable tubular insert 22E and the reusable outer sleeve 24E. In particular, a proximal portion of the disposable tubular insert 22E has a pair of diametrically opposed lateral projections or studs 66, 68, and a proximal portion of the reusable outer sleeve 24E has an expandable section comprising a pair of opposing deflectable flaps 70, 72 with channels 71 and holes 73 for receiving the projections 66, 68. When the outer sleeve 24E is advanced proximally over the outer surface of the tubular insert 22E during initial assembly of the syringe 20E, the projections 66, 68 slide into the channels 71 and ultimately settle into the holes 73 to detachably secure the sleeve 24E to the insert 22E. This holds the sleeve 24E and insert 22E together in an axially and rotationally locked manner. The sleeve 24E and the insert 22E can be separated from each other after the syringe 20E is used by depressing the squeeze tabs 75, which flexes the flaps 70, 72 outward and disengages the holes 73 from the projections 66, 68. The sleeve 24E and the insert 22E can then be pulled apart.

Figure 12:
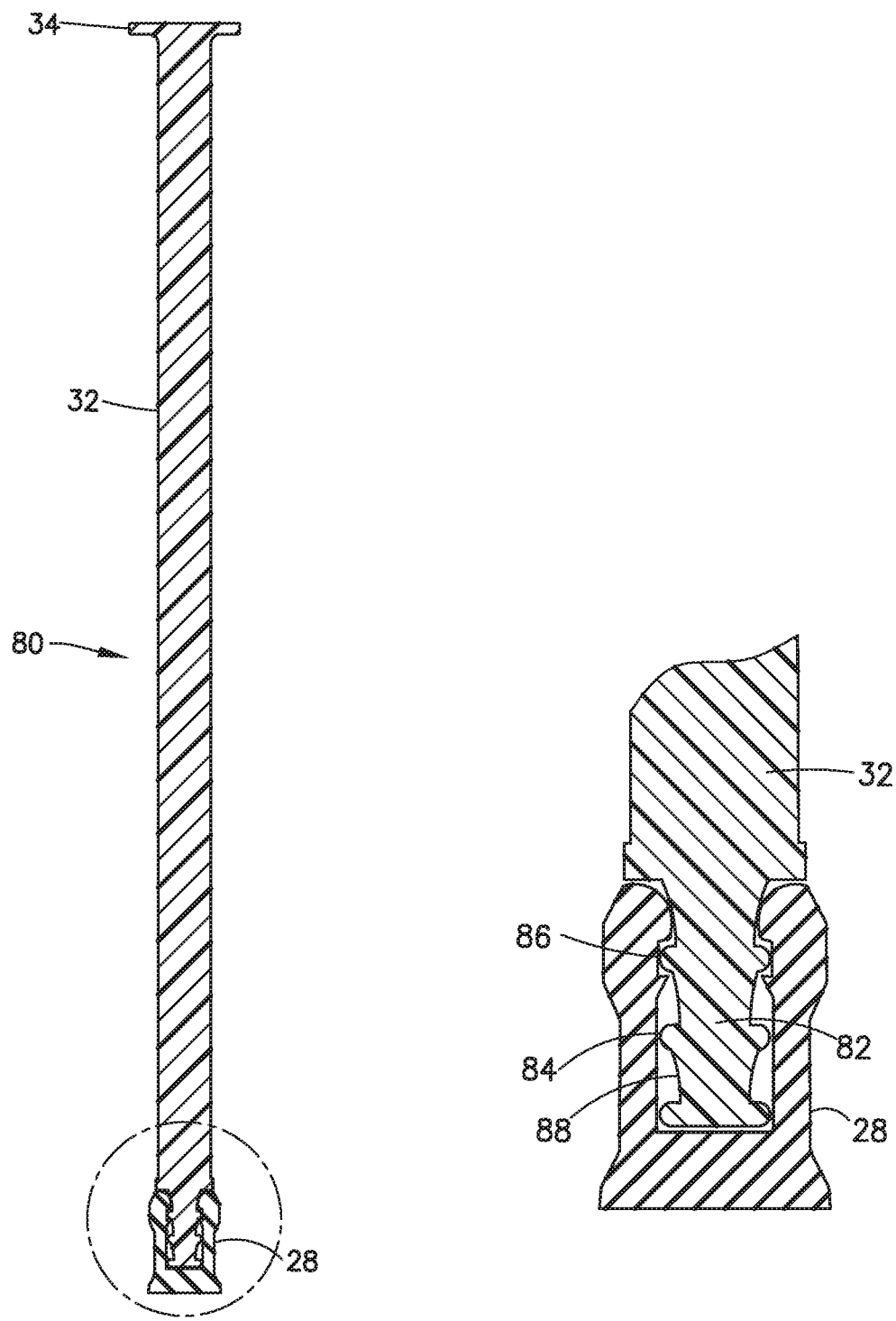
FIGS. 12 and 13 illustrate two different embodiments of a stopper and reusable plunger assembly for use in any of the previous syringe embodiments, or in a conventional syringe.
Figure 13:
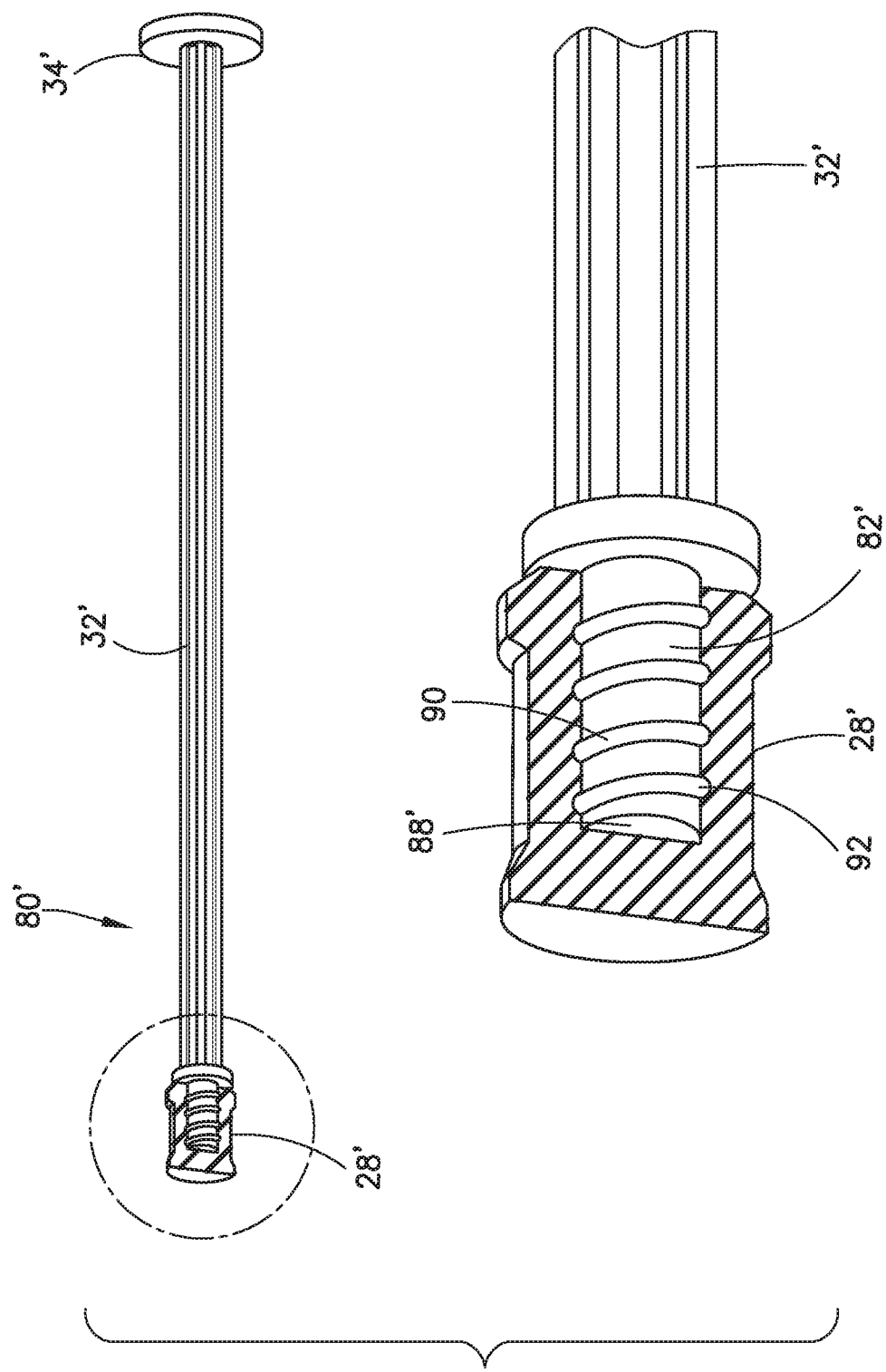

FIGS. 12 and 13 illustrate two different embodiments of a stopper and reusable plunger assembly 80, 80' for use in any of the previous syringe embodiments (i.e., in combination with a disposable insert 22 and a reusable outer sleeve 24) or for use in a conventional single-use syringe with no other reusable components. In each of FIGS. 12 and 13, the plunger 32, 32' is a durable plastic component which can be separated from the rubber stopper 28, 28' after the syringe is used, and then reused as part of another syringe. Such reuse does not compromise the sterility of the syringe, because the plunger 32, 32' does not come into contact with body fluids or with the fluid being transferred by the syringe.

The separation of the plunger 32, 32' from the stopper 28, 28' can be initiated by the user in various ways, depending on the nature of the structural connection between these components. For example, if the distal end 82 of the plunger 32 is provided with external annular rings 84 that mate with internal annular grooves 86 in the stopper cavity 88 as illustrated in FIG. 12, the separation can be achieved by forcefully pulling on the plunger 32 in the proximal direction while the stopper 28 is held in the insert 22 either by the user manually blocking the proximal opening of the insert 22 or by providing a constriction at the proximal opening of the insert 22 (the stopper 28 can be forced past this constriction during initial assembly). Alternatively, if the if the distal end 82' of the plunger 32' is provided on its outside surface with a raised helical screw thread 90 that mates with an internal helical groove 92 in the stopper cavity 88' as illustrated in FIG. 13, the separation can be achieved by simply unscrewing the plunger 32' from the stopper 28'. The friction of the stopper 28' within the insert 22 will ordinarily provide enough resistance to rotation of the stopper 28' to allow the plunger 32' to be unscrewed from it, but if this is not the case, the user can apply manual pressure to the stopper 28' through the walls of the insert 22 and/or sleeve 24 to increase the friction. Such application of pressure can also be used to assist in restraining the stopper 28 when the plunger 32 is removed by axial pulling in the embodiment of FIG. 12.

In all of the embodiments described, the stopper 28 is preferably located at the most proximal end of the insert 22 prior to use. This positioning can be seen, for example, in FIGS. 9B and 9C. The user can push the stopper 28 distally with the plunger tip where it bottoms out and engages with the plunger tip. Additionally, there may be lubricant on the inside of the insert 22 to aid the movement of the stopper 28. Having the stopper 28 initially located at the proximal end of the insert 22 will aid lubricant migration within the insert as well.

FIG. 14 illustrates one possible way in which syringes 20 constructed in accordance with any of the foregoing embodiments may be packaged for use or sale. In the illustrated example, a plurality of inserts 22 (e.g., 10 inserts) having individual stoppers 28 but lacking some or all of the scale markings required for proper use of the syringes is packaged in a sealed plastic bag 100 along with a single reusable sleeve 24 and a single reusable plunger 32. After opening the bag, the user couples the sleeve 24 and plunger 32 (and a separately provided needle or cannula, if required for the intended use) to one of the inserts 22 to form a first syringe 20, uses the first syringe 20, removes the sleeve 24 and plunger 32, and discards the insert 22 (including the stopper 28). The removed sleeve 24 and plunger 32 are then attached to another insert 22 to form a second syringe 20, which is used and subsequently disassembled in the same way. This process is repeated until the supply of inserts 22 is exhausted, at which point the sleeve 24 and plunger 32 may also be discarded.

It will be apparent that variations are possible in which only one of the sleeve 24 and plunger 32 is reusable, in which case the other component is either provided separately for each insert 22 (as in the case where the plunger 32 is not reused) or is not provided at all (as in the case where the inserts 22 are provided with scale markings directly and do not require a separate outer sleeve 24). It will also be apparent that variations are possible in which more than one reusable sleeve 24 and/or plunger 32 is provided in the bag 100 (e.g., two or more reusable outer sleeves 24 with different types of scale markings 44 for different types of insulin), and in which a box or other form of packaging is substituted for the bag 100. The ratio of disposable to reusable components could be higher than 10:1 (e.g., 50:1, 100:1 or higher), and the reusable components could also be packaged separately from the disposable components if desired.

Syringes 20 constructed in accordance with the present invention may be used in any application in which it is desired to inject, withdraw or otherwise transfer fluids. These applications include the administration of insulin and other liquid medications, the withdrawal of blood and other body fluids for sampling purposes, and the transfer of fluids for non-medical purposes.

Although only a few embodiments of the present invention have been shown and described, the present invention is not limited to the described embodiments. Instead, it will be appreciated by those skilled in the art that changes may be made to these embodiments without departing from the scope of the invention. In addition, any of the embodiments, features and/or elements disclosed herein may be combined with one another to form various additional combinations not specifically disclosed, as long as the embodiments, features and/or elements being combined do not contradict each other. All such changes and combinations are considered to be within the scope of the invention as defined by the appended claims and their equivalents.

The invention claimed is:

1. A syringe comprising:
    a barrel assembly comprising a disposable tubular insert having a distally facing cavity and a reusable outer sleeve, the tubular insert forming a fluid reservoir and having a fluid opening at a distal end thereof, the reusable outer sleeve being detachably received on the tubular insert and having visible scale markings thereon, wherein a proximal portion of the reusable outer sleeve has a proximally facing attachment collar for detachable insertion into and retention by the cavity;
    a stopper movably received in the tubular insert for sealing a proximal end of the tubular insert and for displacing fluid into or out of the tubular insert through the fluid opening upon movement of the stopper within the tubular insert; and
    a user-operable plunger coupled to the stopper for causing the stopper to move within the tubular insert and thereby displace the fluid into or out of the tubular insert through the fluid opening under the control of the user.

2. The syringe of claim 1, wherein the attachment collar has flexible arms that engage recesses in the distally facing cavity.

3. The syringe of claim 1, wherein a proximal portion of the disposable tubular insert and a proximal portion of the reusable outer sleeve are each formed with adjoining portions of a flange that can be held by a user's fingers when operating the plunger.

4. The syringe of claim 1, wherein the plunger is detachably coupled to the stopper to allow reuse of the plunger.

5. The syringe of claim 1, further comprising a Luer connector at the fluid opening of the disposable tubular insert.

6. The syringe of claim 1, further comprising a hollow needle or cannula at the fluid opening of the disposable tubular insert.

7. The syringe of claim 1, further comprising a lengthwise slot or window in the reusable outer sleeve through which a fluid level in the disposable tubular insert can be viewed.

8. The syringe of claim 1, wherein the distal facing cavity of the disposable tubular insert includes a detent, and where the attachment collar comprises flexible arms for coupling with a respective detent.

9. A method for performing first and second fluid transfers, comprising:
    performing a first fluid transfer using a first syringe constructed as set forth in claim 1;
    after the first fluid transfer is complete, removing the reusable outer sleeve from the disposable insert of the first syringe and attaching it to the disposable insert of a second syringe, the second syringe being constructed as set forth in claim 1 but lacking a reusable outer sleeve; and
    performing a second fluid transfer using the second syringe having the reusable outer sleeve of the first syringe.

10. A syringe comprising;
    a barrel assembly comprising a disposable tubular insert having a distally facing cavity and a reusable outer sleeve, the tubular insert forming a fluid reservoir and having a fluid opening at a distal end thereof, the reusable outer sleeve being detachably received on the tubular insert and having visible scale markings thereon; wherein a proximal portion of the disposable tubular insert has one or more lateral projections, and wherein a proximal portion of the reusable outer sleeve has an expandable section that is releasably engaged by said one or more lateral projections of the disposable tubular insert to detachably secure the sleeve to the insert;

a stopper movably received in the tubular insert for sealing a proximal end of the tubular insert and for displacing fluid into or out of the tubular insert through the fluid opening upon movement of the stopper within the tubular insert; and a user-operable plunger coupled to the stopper for causing the stopper to move within the tubular insert and thereby displace fluid into or out of the tubular insert through the fluid opening under the control of the user.

11. The syringe of claim 10, wherein said one or more lateral projections comprise two diametrically opposed lateral projections.

12. The syringe of claim 10, wherein the expandable section of the sleeve comprises a pair of opposing deflectable flaps.

13. The syringe of claim 10, wherein the proximal portion of the disposable tubular insert also includes one or both of a flange that can be held by a user's finger when operating the plunger, and an annular collar beneath a thumb press of the plunger.

14. The syringe of claim 10, wherein the lateral projections comprise a detent and the expandable section of the outer sleeve comprise opposing deflectable flaps having channels and holes for receiving the projections.

* * * * *